(12) United States Patent
Cohen et al.

(10) Patent No.: US 9,516,877 B2
(45) Date of Patent: Dec. 13, 2016

(54) ANTIMICROBIAL ALCOHOL FOAM COMPOSITIONS AND METHODS OF PREPARATION

(71) Applicant: GOJO INDUSTRIES, INC., Akron, OH (US)

(72) Inventors: Mitchell Jared Cohen, Salisburg, NC (US); James Harvey Eberts, III, North Canton, OH (US); Evan David Hillman, North Canton, OH (US)

(73) Assignee: GOJO INDUSTRIES, INC., Akron, OH (US)

( * ) Notice: Subject to any disclaimer, the term of this patent is extended or adjusted under 35 U.S.C. 154(b) by 0 days.

(21) Appl. No.: 14/387,989

(22) PCT Filed: Mar. 15, 2013

(86) PCT No.: PCT/US2013/032055
§ 371 (c)(1),
(2) Date: Sep. 25, 2014

(87) PCT Pub. No.: WO2013/147313
PCT Pub. Date: Oct. 3, 2013

(65) Prior Publication Data
US 2015/0080478 A1    Mar. 19, 2015

Related U.S. Application Data (60) Provisional application No. 61/617,987, filed on Mar. 30, 2012.

(51) Int. Cl.
| | | |
|---|---|---|
| *A61K 31/45* | (2006.01) | |
| *A01N 25/16* | (2006.01) | |
| *A61K 8/34* | (2006.01) | |
| *A61K 8/04* | (2006.01) | |
| *A61K 8/365* | (2006.01) | |
| *A61Q 17/00* | (2006.01) | |
| *A61K 8/86* | (2006.01) | |
| *A61K 8/19* | (2006.01) | |
| *A01N 31/02* | (2006.01) | |
| *A01N 37/02* | (2006.01) | |
| *A01N 59/00* | (2006.01) | |
| *A01N 61/00* | (2006.01) | |

(52) U.S. Cl.
CPC ............ *A01N 25/16* (2013.01); *A01N 31/02* (2013.01); *A01N 37/02* (2013.01); *A01N 59/00* (2013.01); *A01N 61/00* (2013.01); *A61K 8/046* (2013.01); *A61K 8/19* (2013.01); *A61K 8/34* (2013.01); *A61K 8/342* (2013.01); *A61K 8/365* (2013.01); *A61K 8/86* (2013.01); *A61Q 17/005* (2013.01)

(58) Field of Classification Search
USPC ........................................................ 514/724
See application file for complete search history.

(56) References Cited

U.S. PATENT DOCUMENTS

| 4,487,757 A | * | 12/1984 | Kiozpeoplou ............ A61K 8/02 |
| | | | 424/44 |
| 5,047,166 A | | 9/1991 | Well |
| 5,154,917 A | | 10/1992 | Ibrahim et al. |
| 5,167,950 A | * | 12/1992 | Lins ........................ A01N 25/16 |
| | | | 424/47 |
| 5,223,245 A | | 6/1993 | Ibrahim et al. |
| 5,455,035 A | | 10/1995 | Guerrero et al. |
| 5,804,546 A | | 9/1998 | Hall |
| 5,902,225 A | | 5/1999 | Monson |
| 5,948,439 A | | 9/1999 | Forman et al. |
| 5,955,057 A | | 9/1999 | Maunder et al. |
| 6,177,092 B1 | | 1/2001 | Lentini et al. |
| 6,583,103 B1 | | 6/2003 | Klinkhammer |
| 6,696,054 B1 | | 2/2004 | Falanga |
| 2004/0009885 A1 | | 1/2004 | Davies et al. |
| 2007/0027119 A1 | | 2/2007 | Ahmed et al. |
| 2007/0065383 A1 | * | 3/2007 | Fernandez de Castro ............ |
| | | | A01N 25/06 |
| | | | 424/70.1 |
| 2007/0154402 A1 | | 7/2007 | Trumbore |
| 2008/0207767 A1 | | 8/2008 | Dobos et al. |
| 2008/0277421 A1 | | 11/2008 | Zlatic et al. |
| 2010/0172848 A1 | | 7/2010 | Modak et al. |
| 2011/0189307 A1 | | 8/2011 | Bartels |

FOREIGN PATENT DOCUMENTS

| FR | 2477414 A1 | 9/1981 |
| FR | 2738148 A1 | 8/1995 |
| WO | 2005030917 A1 | 4/2005 |
| WO | 2007068553 A1 | 6/2007 |
| WO | 2008041045 A1 | 4/2008 |
| WO | 2010080835 A1 | 7/2010 |
| WO | WO 2010/125470 | * 11/2010 ............ A61K 9/12 |
| WO | 2011013008 A2 | 2/2011 |
| WO | 2011013008 A2 | 5/2011 |

OTHER PUBLICATIONS

Drake D. Antibacterial activity of baking soda. Compend Contin Educ Dent Suppl. 1997;18(21):S17-21.*
Nakatsuji T, Kao MC, Fang JY, Zouboulis CC, Zhang L, Gallo RL, Huang CM. Antimicrobial property of lauric acid against Propionibacterium acnes: its therapeutic potential for inflammatory acne vulgaris. J Invest Dermatol. Oct. 2009;129(10):2480-8. Epub Apr. 23, 2009.*
International Search Report and Written Opinion dated Jul. 5, 2013 for PCT/US2013/032055.

* cited by examiner

*Primary Examiner* — Rei-Tsang Shiao
(74) *Attorney, Agent, or Firm* — Renner Kenner Greive Bobak Taylor and Weber (57) ABSTRACT

A method for preparing an antimicrobial alcoholic foam composition by combining two or more pre-mix compositions. A first pre-mix composition is primarily alcoholic comprises an alcohol, an acidic component, and a waxy component. A second pre-mix composition is primarily aqueous comprises water and a carbonate. An antimicrobial alcoholic foam composition that does not require added air or aerosol propellant is also provided.

42 Claims, 2 Drawing Sheets

ANTIMICROBIAL ALCOHOL FOAM COMPOSITIONS AND METHODS OF PREPARATION

TECHNICAL FIELD

Embodiments of the present invention provide antimicrobial alcohol foam compositions and methods for producing antimicrobial alcohol foam compositions.

BACKGROUND OF THE INVENTION

There is a need in healthcare settings for efficacious broad-spectrum antimicrobial disinfection products. Foam cleaning products are popular, in part because they are easier to spread on surfaces. Consumers seem to prefer the luxury of foamed soap and disinfecting products. Less foam is needed to produce the same cleaning power as liquids or gels, due at least partly to the higher surface area of the foam. Properly formulated foam products do not produce the drip and splash that is experienced with traditional gelled or liquid products, because the formulation is not dispensed in a liquid state. This prevents damage to the floors and walls of facilities where the product dispensers are used. Manufacturing of foam products may be easier than gelled products, which often incorporate powdered thickeners that are difficult to handle.

Typically, foam products require dispensers that are adapted to mix a gas with a liquid in order to produce a foam. Aerosol foam products require a pressurized system and a propellant. U.S. Pat. No. 6,660,282 describes some of the drawbacks of non-aerosol foam products. The '282 patent states that certain types of non-aerosol dispensers operate with porous filters or meshed screens, and therefore are not tolerant to particulate components or to even modestly viscous compositions. The '282 patent also states that non-aerosol generated foams often lack a dense luxurious character and often do not provide a cushioned afterfeel.

Thus, there is a need for widely-applicable antimicrobial alcohol foam compositions that do not require a dispenser to mix a gas with a liquid in order to produce the foam.

SUMMARY OF THE INVENTION

Embodiments of the present invention provide antimicrobial alcohol foam compositions and methods for producing antimicrobial alcohol foam compositions without adding air, and without the need for pressurized components or aerosol propellants. Pre-mix compositions, which may be stored separately in non-pressurized containers, form carbon dioxide when combined, which in conjunction with the other components of the pre-mix compositions forms an antimicrobial alcohol foam composition.

According to embodiments of the present invention, an antimicrobial alcoholic foam composition is obtainable from mixing (a) a first pre-mix composition that comprises at least about 50 wt. % of a lower alcohol, based upon the total weight of the first pre-mix composition, an acidic component, and a waxy component, and (b) a second pre-mix composition that comprises water and a carbonate.

Embodiments of the present invention provide a carbon dioxide-based antimicrobial alcoholic foam composition, wherein the foam comprises $C_{1-6}$ alcohol, a waxy component, and optional ingredients, but does not contain any added air or aerosol propellant.

In one or more embodiments, the present invention provides a method for preparing an antimicrobial alcoholic foam composition, the method comprising the step of combining (a) a first pre-mix composition that comprises at least about 50 wt. % of a lower alcohol, based upon the total weight of the first pre-mix composition, an acidic component, and a waxy component, and (b) a second pre-mix composition that comprises water and a carbonate.

In one or more embodiments, the present invention provides a method of preparing an antimicrobial alcoholic foam composition, the method comprising the steps of providing a dispenser having a first reservoir containing a first liquid pre-mix that is an aqueous pre-mix, a second reservoir containing a second liquid pre-mix that is an alcoholic pre-mix; dispensing an aliquot of said aqueous pre-mix, wherein said aqueous pre-mix comprises a carbonate and water; dispensing an aliquot of said alcoholic pre-mix, wherein said alcoholic pre-mix comprises at least about 50 wt. % of a $C_{1-6}$ alcohol, based upon the total weight of the alcoholic pre-mix, a waxy component, and an acidic component; commingling said aliquot of said aqueous pre-mix and said aliquot of said alcoholic pre-mix, whereupon said aliquots of said aqueous pre-mix and said alcoholic pre-mix chemically react and generate an antimicrobial alcoholic foam.

In one or more embodiments, the present invention provides a self-generated foam prepared by combining an alcoholic pre-mix comprising at least about 50 wt. % of a lower alcohol, based upon the total weight of the alcoholic pre-mix, at least one acidic component, and at least one waxy component; and an aqueous pre-mix comprising a carbonate.

In any of the above embodiments, or as further described herein, the acidic component may be hydrochloric acid, nitric acid, phosphoric acid, phosphonic acid, boric acid, sulfuric acid, adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, and 2,5 furandicarboxylic acid, tartaric acid, malic acid, gluconic acid, fumaric acid, ascorbic acid, citric acid, isocitric acid, lactic acid, tartronic acid, oxalic acid, salicylic acid, malonic acid, potassium bitartrate, calcium phosphate, sodium aluminum phosphate, sodium aluminum sulfate, monosodium phosphate, disodium pyrophosphate, calcium lactate, calcium sulfate, calcium phosphate, sodium aluminum phosphate, sodium aluminum sulfate, monosodium phosphate and disodium pyrophosphate, or a mixture thereof.

In any of the above embodiments, or as further described herein, the acidic component may be citric acid, lactic acid, malic acid, tartaric acid, salicylic acid, oxalic acid, or a mixture thereof.

In any of the above embodiments, or as further described herein, the acidic component may be citric acid.

In any of the above embodiments, or as further described herein, the amount of acidic component may be at least about 0.02 equivalent weights of acid per 100 g of combined aqueous pre-mix and alcoholic pre-mix.

In any of the above embodiments, or as further described herein, the amount of acidic component may be from 0.5 to about 2 times the number of equivalent weights of carbonate present in the aqueous pre-mix.

In any of the above embodiments, or as further described herein, the amount of acidic component may be the stoichiometric amount of acid required to produce at least about 0.02 moles of carbon dioxide per 100 g of combined aqueous pre-mix and alcoholic pre-mix.

In any of the above embodiments, or as further described herein, the carbonate may be sodium carbonate, potassium carbonate, lithium carbonate, sodium bicarbonate, potassium bicarbonate, calcium bicarbonate, ammonium bicarbonate, or a mixture thereof.

In any of the above embodiments, or as further described herein, the carbonate may be potassium bicarbonate.

In any of the above embodiments, or as further described herein, the amount of carbonate may be an effective amount.

In any of the above embodiments, or as further described herein, the amount of carbonate may be the stoichiometric amount of carbonate required to yield at least about 0.02 moles of carbon dioxide per 100 g of combined aqueous pre-mix and alcoholic pre-mix.

In any of the above embodiments, or as further described herein, the aqueous pre-mix may be a saturated solution with respect to the carbonate.

In any of the above embodiments, or as further described herein, the waxy component may be an emulsifying wax.

In any of the above embodiments, or as further described herein, the waxy component may be present in an amount of at least about 0.2 wt. %, based upon the total weight of the alcoholic pre-mix.

In any of the above embodiments, or as further described herein, the waxy component may be present in an amount of at least about 0.1 wt. %, based upon the total weight of the combined alcoholic pre-mix and aqueous pre-mix.

In any of the above embodiments, or as further described herein, the aqueous pre-mix may further comprise an emulsifier selected from the group consisting of polysorbate, poloxamer, polyethoxylated siloxane polymer, or a mixture thereof.

In any of the above embodiments, or as further described herein, the alcoholic pre-mix may further comprise an emulsifier selected from the group consisting of polysorbate, poloxamer, polyethoxylated siloxane polymer, or a mixture thereof.

In any of the above embodiments, or as further described herein, the emulsifier may be a poloxamer.

In any of the above embodiments, or as further described herein, the aqueous pre-mix may further comprise up to about 49 wt. % $C_{1-6}$ alcohol.

In one or more embodiments, or as further described herein, the foam volume is 1.5 to 5 times the combined liquid volume of the aqueous pre-mix and the alcoholic pre-mix.

In one or more embodiments, or as further described herein, the foam is stable for at least about 1 minute at room temperature and pressure.

DETAILED DESCRIPTION OF ILLUSTRATIVE EMBODIMENTS

In one or more embodiments, the present method provides an antimicrobial alcoholic foam composition. In addition to being effective as a hand sanitizer, the antimicrobial composition of the present invention may be employed on a wide variety of surfaces or substrates, including skin, porous, and non-porous surfaces.

The antimicrobial alcoholic foam composition may be prepared by combining two or more liquid pre-mix compositions. A first composition, which is primarily alcoholic and is therefore referred to herein as an alcoholic pre-mix, comprises an alcohol, an acidic component, and a waxy component. A second composition, which is primarily aqueous and is therefore referred to herein as an aqueous pre-mix, comprises water and a carbonate.

In one or more embodiments, any of a wide variety of acids may be employed, so long as the acid is capable of reacting with a carbonate to produce carbon dioxide ($CO_2$). Examples of acids include mineral acids and organic acids. Mineral acids include, without limitation, hydrochloric acid, nitric acid, phosphoric acid, phosphonic acid, boric acid, and sulfuric acid. Organic acids include sulfonic acids, organophosphorus acids, carboxylic acids such as benzoic acids, propionic acids, phthalic acids, butyric acids, acetic acids, amino acids, and other substituted and unsubstituted organic acids.

Examples of organic acids include adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxoglutaric acid, dl-glyceric acid, and 2,5 furandicarboxylic acid.

In certain embodiments, the acid includes a carboxylic acid. Examples of carboxylic acids include tartaric acid, malic acid, gluconic acid, fumaric acid, ascorbic acid, citric acid, isocitric acid, lactic acid, tartronic acid, oxalic acid, salicylic acid, malonic acid, and mixtures thereof.

In one or more embodiments, the acid component may be an acid sodium, potassium or calcium salt. Examples of useful salts include potassium bitartrate, calcium phosphate, sodium aluminum phosphate, sodium aluminum sulfate, monosodium phosphate, disodium pyrophosphate, calcium lactate, calcium sulfate, calcium phosphate, sodium aluminum phosphate, sodium aluminum sulfate, monosodium phosphate and disodium pyrophosphate.

In one or more embodiments, the waxy component may be a lipophilic fatty compound that is solid at room temperature (25° C.) and atmospheric pressure (760 mmHg, i.e. 101 kPa). Typically, the waxy component has a melting point greater than 40° C. In one or more embodiments, the waxy component is characterized by an anisotropic crystal organization in its solid state. Many waxes are capable of undergoing a reversible solid/liquid change of state. Generally, the waxy component is insoluble in water. In one or more embodiments, the waxy component may be selected from natural waxes, synthetic waxes, and emulsifying waxes. Examples of waxes include polyethylene waxes derived from ethylene (co)polymerisation, waxes obtained by Fischer-Trops synthesis, fatty alcohols, fatty acid esters, glycerides, silicone waxes, and mixtures thereof.

In one or more embodiments, the waxy component should exhibit at least a minimal amount of solubility in a $C_{1-6}$ alcohol. In one or more embodiments, the waxy component has a solubility of at least about 2 grams waxy component per 93 grams $C_{1-6}$ alcohol. In other embodiments, the waxy component has a solubility of at least about 4 grams waxy component per 91 grams $C_{1-6}$ alcohol, in other embodiments at least about 5 grams waxy component per 90 grams $C_{1-6}$ alcohol, and in still other embodiments at least about 6 grams waxy component per 89 grams $C_{1-6}$ alcohol.

Examples of useful waxes include emulsifying waxes. In general, while waxes per se are substantially hydrophobic, emulsifying waxes include waxes that have been chemically treated and/or blended with additional ingredients in order to enhance the ability of the wax to act as an emulsifier. Emulsifying waxes that comply with the standards of the National Formulary are sometimes referred to as emulsifying wax NF. Examples of emulsifying waxes include blends of one or more fatty alcohol and one or more emulsifying agent.

In one or more embodiments, the waxy component is selected from the group consisting of beeswax, carnauba wax, candelilla wax, ouricury wax, Japan wax, cork fiber wax, sugarcane wax, paraffin waxes, lignite waxes, microcrystalline waxes, lanolin wax, ozokerite, polyethylene wax, silicone waxes, plant waxes, $C_{8-24}$ fatty alcohols, $C_{8-24}$ fatty acids, glycerides that are solid at room temperature, blends of a $C_{8-24}$ fatty alcohol with an ethoxylated $C_{8-24}$ fatty alcohol, blends of a $C_{8-24}$ fatty alcohol and a non-ionic surfactant, and mixtures thereof. In one or more embodiments, the waxy component includes capryl alcohol, pelargonic alcohol, decyl alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, isostearyl alcohol, oleyl alcohol, linoleyl alcohol, linolenyl alcohol, ricinoleyl alcohol, nonadecyl alcohol, arachidyl alcohol, heneicosyl alcohol, behenyl alcohol, erucyl alcohol, lignoceryl alcohol, cetearyl alcohol, or a combination thereof. In one or more embodiments, the waxy component is a blend that includes cetearyl alcohol and ceteareth 20. In one or more embodiments, the waxy component is a blend that includes cetearyl alcohol and stearyl alcohol. In one or more embodiments, the waxy component is a blend that includes cetearyl alcohol, polysorbate 60, PEG-150 stearate, and steareth-20.

In one or more embodiments, the alcohol is a lower alcohol, i.e. an alcohol containing 1 to 6 carbon atoms. Typically, these alcohols have antimicrobial properties. Examples of lower alcohols include, but are not limited to, methanol, ethanol, propanol, butanol, pentanol, hexanol, and isomers and mixtures thereof. In one or more embodiments, the alcohol comprises ethanol, propanol, or butanol, or isomers or mixtures thereof. In particular embodiments, the alcohol comprises ethanol.

Generally, the alcoholic pre-mix comprises at least about 50 percent by weight (wt. %) $C_{1-6}$ alcohol, based upon the total weight of the alcoholic pre-mix. In one embodiment, the alcoholic pre-mix comprises at least about 60 wt. % alcohol, in another embodiment, the alcoholic pre-mix comprises at least about 70 wt. % alcohol, in yet another embodiment, the alcoholic pre-mix comprises at least about 80 wt. % alcohol, and in another embodiments, the alcoholic pre-mix comprises at least about 90 wt. % alcohol, based upon the total weight of alcoholic pre-mix. More or less alcohol may be required in certain instances, depending particularly on other ingredients and/or the amounts thereof employed in the composition. In certain embodiments, the alcoholic pre-mix comprises from about 50 wt. % to about 99 wt. % $C_{1-6}$ alcohol, in other embodiments, the alcoholic pre-mix comprises from about 60 wt. % to about 98 wt. % of alcohol, in yet other embodiments, the alcoholic pre-mix comprises from about 70 wt. % to about 97 wt. % of alcohol, and in still other embodiments, the alcoholic pre-mix comprises from about 80 wt. % to about 96 wt. % of alcohol, based upon the total weight of the alcoholic pre-mix.

In one or more embodiments, the balance of the alcoholic pre-mix is a $C_{1-6}$ alcohol. In other embodiments, the alcoholic pre-mix may include one or more optional ingredients, with the proviso that there is no deleterious effect on the foaming or antimicrobial efficacy of the antimicrobial foam. In one or more embodiments, the alcoholic pre-mix contains only de minimus amounts of water, if any at all. In one or more embodiments, the alcoholic pre-mix is devoid of water.

In one or more embodiments, the aqueous pre-mix comprises water and a carbonate. It is believed that, upon combination of the aqueous pre-mix and the alcoholic pre-mix, a chemical reaction involving the acid and the basic carbonate produces a gaseous product, such as carbon dioxide.

Suitable carbonates include those that are capable of reacting with an acid to produce carbon dioxide. In one or more embodiments, the carbonate is at least partially soluble in water at standard temperature and pressure. For purposes of this disclosure, it will be understood that hydrogen carbonates also fall within the classification "carbonate." Examples of carbonates include alkali carbonates and alkali and alkaline earth bicarbonates. Particular examples of carbonates include sodium carbonate, potassium carbonate, lithium carbonate, sodium bicarbonate, potassium bicarbonate, calcium bicarbonate, and ammonium bicarbonate.

Although the aqueous pre-mix is primarily water, in one or more embodiments the aqueous pre-mix may contain minor amounts of $C_{1-6}$ alcohol. By minor amounts is meant that the amount of $C_{1-6}$ alcohol does not exceed the amount of water in the aqueous pre-mix. In particular embodiments, the aqueous pre-mix may contain up to about 49 wt. % $C_{1-6}$ alcohol, in other embodiments, up to about 40 wt. %, in other embodiments, up to about 30 wt. %, in other embodiments, up to about 20 wt. %, in other embodiments, up to about 15 wt. % $C_{1-6}$ alcohol, based upon the total weight of the aqueous pre-mix.

In one or more embodiments, the aqueous pre-mix is devoid of $C_{1-6}$ alcohol. In one embodiment, the aqueous pre-mix may contain from zero to about 49 wt. % $C_{1-6}$ alcohol, in other embodiments, from about 0.5 to about 40 wt. % $C_{1-6}$ alcohol, in other embodiments, from about 1 to about 30 wt. % alcohol, based upon the total weight of the aqueous pre-mix.

In one or more embodiments, the balance of the aqueous pre-mix is water. In other embodiments, the aqueous pre-mix may include one or more optional ingredients, with the proviso that there is no deleterious effect on the foaming or antimicrobial efficacy of the antimicrobial foam.

As described hereinabove, the aqueous pre-mix and alcohol pre-mix of this invention include a number of ingredients that combine to produce an antimicrobial alcoholic foam. Either or both of the pre-mixes may further comprise a wide range of optional ingredients, with the proviso that they do not deleteriously affect the foaming or sanitizing efficacy of the compositions. The CTFA International Cosmetic Ingredient Dictionary and Handbook, Eleventh Edition 2005, and the 2004 CTFA International Buyer's Guide, both of which are incorporated by reference herein in their entirety, describe a wide variety of nonlimiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants, conditioners, cosmetic astringents, cosmetic biocides, denaturants, drug astringents, emulsifiers, external analgesics, film formers, fragrance components, humectants, moisturizers, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include sequestrants, keratolytics, topical active ingredients, and the like.

In certain embodiments, the antimicrobial composition comprises one or more humectants. Examples of humectants include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like.

In one or more embodiments, the antimicrobial composition includes one or more emulsifying agents. Examples of emulsifying agents include non-ionic surfactants, ethoxylated fatty alcohols and ethoxylated fatty alcohol esters. In one embodiment, the emulsifying agent is a polysorbate, poloxamer, polyethoxylated siloxane polymer, or a mixture thereof. In one embodiment, the emulsifying agent is sorbitan oleate trideceth-2, polysorbate 60, PEG-150 stearate, steareth-20, ceteareth-20, PEG/PPG-20/6 dimethicone, or a mixture thereof. In one or more embodiment, an emulsifying agent is present in the alcoholic pre-mix. In one or more embodiments, the emulsifying agent is present in an amount of from about 0 to about 10 wt. %, in other embodiments from about 0.1 to about 5 wt. %, in other embodiments from about 0.5 to about 2 wt. %, based upon the total weight of the alcoholic pre-mix. In these or other embodiments, an emulsifying agent is present in the aqueous pre-mix, In one or more embodiments, the emulsifying agent is present in an amount of from about 0 to about 10 wt. %, in other embodiments from about 0.1 to about 5 wt. %, in other embodiments from about 0.5 to about 2 wt. %, based upon the total weight of the aqueous pre-mix.

In one embodiment, the aqueous pre-mix and/or the alcoholic pre-mix includes one or more thickeners and optionally one or more stabilizers. Examples of thickeners and stabilizers include hydroxyethyl cellulose hydroxypropyl cellulose, methyl cellulose, carboxymethyl cellulose, and ammonium acryloyldimethyltaurate/VP copolymer. In one embodiment, where the thickener or stabilizer is starch-based, the thickener or stabilizer is present in an amount of up to about 10 wt. %, in another embodiment in an amount of from about 0.1 to about 5 wt. %, in yet another embodiment from about 0.2 to about 1 wt. %, based upon the total weight of the pre-mix. In other embodiments, where the thickener or stabilizer is a synthetic polymer, the thickener or stabilizer is present in an amount of up to about 15 wt. %, in another embodiment in an amount of from about 0.1 to about 10 wt. %, in yet another embodiment from about 1 to about 2 wt. %, based upon the total weight of the pre-mix.

In one or more embodiments, the antimicrobial composition includes one or more solubilizers. Examples of solubilizers include PEG-40 hydrogenated castor oil, polysorbate-80, PEG-80 sorbitan laurate, ceteareth-20, oleth-20, PEG-4, and propylene glycol. The amount of solubilizer is not particularly limited, so long as it does not deleteriously affect the foaming or antimicrobial efficacy of the composition.

In one or more embodiments, the aqueous pre-mix and/or the alcoholic pre-mix includes one or more antiviral agents or antiviral enhancers. Examples of antiviral agents include botanicals such as rosmarinic acid, tetrahydrocurcuminoids, oleuropen, oleanolic acid, *aspalathus linearis* extract, white tea, red tea, green tea extract, neem oil limonoids, coleus oil, licorice extract, burnet, ginger & cinnamon extracts, alpha-glucan oligosaccharide, *perilla ocymoides* leaf powder, camphor, *camellia oleifera* leaf extract, ginger, menthol, *eucalyptus*, capillisil hc, hydroxyprolisilane cn, sandlewood oil/resin, *calendula* oil, rosemary oil, lime/orange oils, and hop acids. When used, the antiviral agents are present in amounts of from about 0.1 to about 1 percent by weight, based upon the total weight of the pre-mix.

Examples of antiviral enhancers include cationic oligomers and polymers, chaotropic agents, and copper and zinc compounds. Antiviral enhancers are further described in U.S. Pat. No. 8,119,115 and co-pending U.S. Patent Application Publications 2007/0185216, and 2009/0018213, all of which are hereby incorporated by reference.

It is envisioned that, in one or more embodiments, auxiliary antimicrobial agents could be included, with the proviso that the antimicrobial ingredient does not deleteriously affect the sanitizing properties of the composition. In other embodiments, one or more auxiliary antimicrobial agents may be present in the aqueous pre-mix, in the alcohol pre-mix, or in both. Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidiamide; 2-bromo-2-nitropropane-1,3-diol; $C_{6-10}$ alkane diols, including 1,2-octanediol; benzalkonium chloride; cetylpyridinium chloride; alkylbenzyldimethylammonium chlorides; iodine; phenol; bisphenol; diphenyl ether; phenol derivatives; povidone-iodine including polyvinylpyrrolidinone-iodine; parabens; hydantoins and derivatives thereof, including 2,4-imidazolidinedione and derivatives of 2,4-imidazolidinedione as well as dimethylol-5,5- dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; lauric arginate (LAE), benzethonium chloride; methylbenzethonium chloride; glyceryl laurate; transition metal compounds such as silver, copper, magnesium, zinc compounds; hydrogen peroxide; chlorine dioxide; anilides; bisguanidines; tropolone; and mixtures thereof. Auxiliary antimicrobial agents and antimicrobial enhancers are further described in co-pending U.S. application Ser. No. 13/377,839 and International patent application publication no. WO 2011/119517, both of which are incorporated herein by reference.

In one or more embodiments the amount of acid, waxy component, carbonate, and other ingredients may be expressed based upon the combined amount of aqueous pre-mix and alcoholic pre-mix.

In one or more embodiments, the amount of acid may be expressed on an acid equivalent weight basis, relative to the combined amount of aqueous pre-mix and alcoholic pre-mix, where the equivalent weight of an acid is the weight that contains one atomic weight of acidic hydrogen, i.e., hydrogen that reacts during a neutralization of acid with base. In one or more embodiments, the amount of acid is at least about 0.02 equivalent weights of acid per 100 grams (g) of combined aqueous pre-mix and alcoholic pre-mix. In other embodiments, the amount of acid is at least about 0.04, in other embodiments at least about 0.05, and in other embodiments, at least about 0.075 equivalent weights per 100 grams (g) of combined aqueous pre-mix and alcoholic pre-mix. It will be understood that higher amounts of acid may be used.

In one or more embodiments, the amount of acid may be expressed on a stoichiometric basis, relative to the amount of carbonate. In particular embodiments, the number of equivalent weights of acid present in the alcoholic pre-mix is from about 0.5 to about 2, in other embodiments from about 0.6 to about 1.5, in other embodiments from about 0.8 to about 1.2 times the number of equivalent weights of carbonate present in the aqueous pre-mix.

In these or other embodiments, the amount of acid may be expressed on a stoichiometric basis, relative to the amount of carbon dioxide to be produced when the aqueous pre-mix and the alcoholic pre-mix are combined. In particular embodiments, the number of equivalent weights of acid is the stoichiometric amount of acid required to produce at least about 0.02 moles of carbon dioxide per 100 grams (g) of combined aqueous pre-mix and alcoholic pre-mix. In other embodiments, the amount of acid is the stoichiometric amount of acid required to produce at least about 0.04, in other embodiments at least about 0.05, and in other embodiments, at least about 0.075 moles of carbon dioxide per 100 grams (g) of combined aqueous pre-mix and alcoholic pre-mix.

In one or more embodiments, the amount of waxy component is not particularly limited, but may be selected based upon such factors as aesthetic preferences and solubility parameters. In one or more embodiments, the amount of waxy component may be expressed relative to the total weight of alcoholic pre-mix. In these or other embodiments, the amount of waxy component is at least about 0.2 wt. %, in other embodiments at least about 0.5 wt. %, in other embodiments at least about 0.8 wt. %, based upon the total weight of the alcoholic pre-mix. In these or other embodiments, the amount of waxy component is from about 0.2 to about 10 wt. %, in other embodiments from about 0.5 to about 8 wt. %, in other embodiments from about 0.8 to about 6 wt. %, based upon the total weight of the alcoholic pre-mix.

In one or more embodiments, the amount of waxy component may be expressed relative to the total weight of combined aqueous pre-mix and alcoholic pre-mix. In these or other embodiments, the amount of waxy component is from about 0.1 to about 8 wt. %, in other embodiments from about 0.2 to about 5 wt. %, in other embodiments from about 0.4 to about 4 wt. %, based upon the total weight of the combined aqueous pre-mix and alcoholic pre-mix.

It will be understood that some carbonates have limited solubility in aqueous solvents, and the maximum amount of carbonate may be defined by the solubility limits at standard temperature and pressure. In one or more embodiments, the solubility of the carbonate in water at 20° C. is at least about 20 grams per 100 milliliters of water, in other embodiments, at least about 50 grams per 100 milliliters of water.

In one or more embodiments, the minimum amount of carbonate may be defined as an effective amount to produce a foam. In one or more embodiments, the effective amount of carbonate may be expressed relative to the amount of carbon dioxide to be produced when the aqueous pre-mix and the alcoholic pre-mix are combined. In one embodiment, the effective amount of carbonate may be calculated as the amount of carbonate required to yield at least about 0.02 moles of $CO_2$, per 100 g of combined aqueous pre-mix and alcoholic pre-mix, in other embodiments, at least about 0.04 moles of $CO_2$, in other embodiments, at least about 0.05 moles of $CO_2$, and in other embodiments, at least about 0.075 moles $CO_2$, per 100 g of the combined aqueous pre-mix and alcoholic pre-mix. In one or more embodiments, the aqueous pre-mix is a saturated solution with respect to the carbonate, at standard temperature and pressure.

In one or more embodiments, the amount of carbonate may be expressed on an equivalent weight basis, relative to the combined amount of aqueous pre-mix and alcoholic pre-mix, where the equivalent weight of carbonate is the mass of carbonate that is stoichiometrically required to produce one mole of carbon dioxide. In one or more embodiments, the amount of carbonate is at least about 0.02 equivalent weights per 100 grams (g) of combined aqueous pre-mix and alcoholic pre-mix. In other embodiments, the amount of carbonate is at least about 0.04, in other embodiments at least about 0.05, and in other embodiments, at least about 0.075 equivalent weights per 100 grams (g) of combined aqueous pre-mix and alcoholic pre-mix.

The pre-mix components may be dispensed from physically separate packages or from a unitary package having non-communicating chambers. For purposes of this specification, the term dispenser apparatus refers to a configuration where multiple liquid components are dispensed from a plurality of physically separate packages, and also refers to a configuration where multiple liquid components are dispensed from a unitary package having a plurality of non-communicating chambers, each chamber having an orifice through which an aliquot of a component is dispensed. Advantageously, it is not necessary to mix air with the liquid aliquots. No aerosol propellant is necessary.

In one or more embodiments, aliquots of the pre-mix components are dispensed substantially simultaneously, such that the liquid aliquots are commingled. In particular embodiments, the aliquots are dispensed through orifices that are configured to enable the commingling of the aliquots. It will be understood that the dispenser may take a variety of forms, and may include a variety of components and configurations in order to cause the desired commingling of aliquots of the pre-mix components and dispensing of a foam product. It is not necessary to use a mesh or screen.

Figure 1:
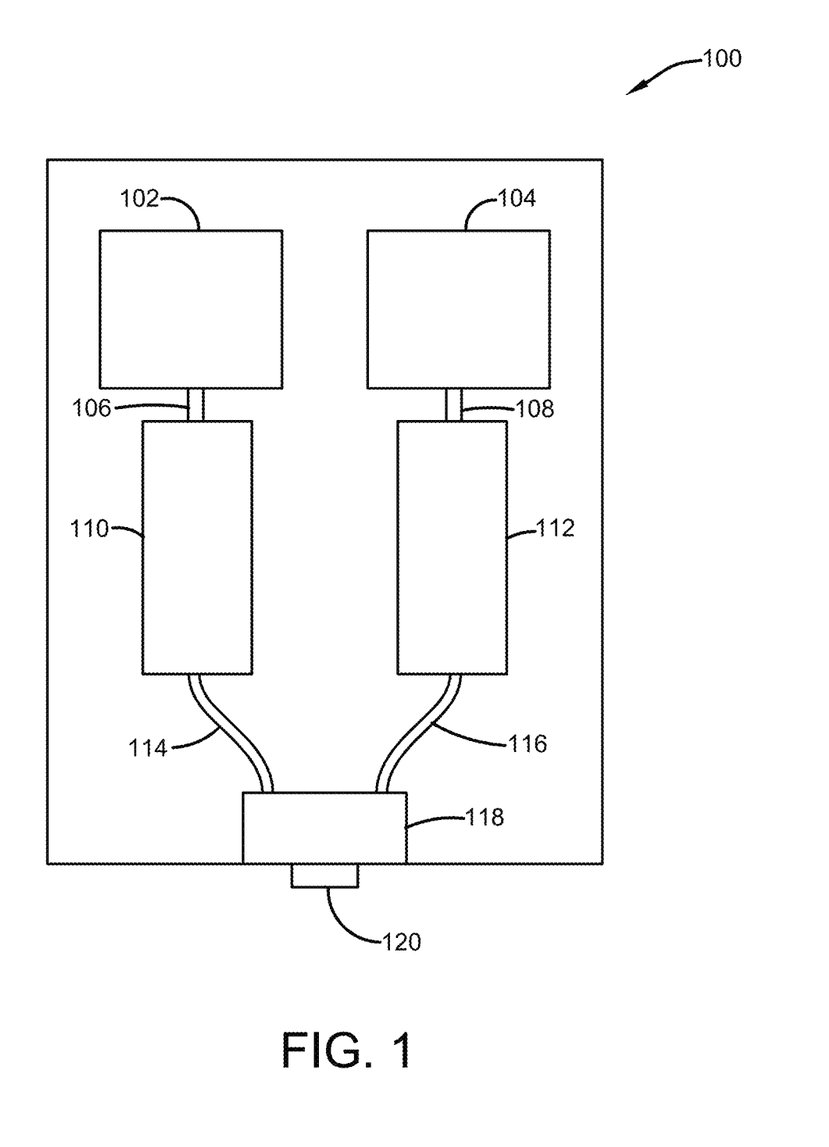
FIG. 1 is a schematic view of a dispenser according to the present invention.

One embodiment of an exemplary dispenser is shown in FIG. 1 and is generally indicated by the numeral 100. Dispenser 100 may include a first reservoir 102 containing a first liquid pre-mix component (e.g. alcoholic pre-mix component), and a second reservoir 104 containing a second liquid pre-mix component (e.g. aqueous pre-mix component). As will be apparent to those skilled in the art, and as indicated above, the first and second reservoirs 102 and 104 are not in direct communication with one another, and the first and second pre-mix components are therefore stored separately within the dispenser. Although separate reservoirs are shown in FIG. 1, it is contemplated that the first and second reservoirs 102 and 104 may be provided as physically separate chambers in a single package. Each of the first and second reservoirs 102 and 104 is impervious to fluid transfer therethrough, except through inlet passages 106 and 108, respectively.

Generally, the present invention provides a method of preparing an antimicrobial alcoholic foam composition, the method comprising the steps of providing a dispenser having a first reservoir containing a first liquid pre-mix that is an aqueous pre-mix, a second reservoir containing a second liquid pre-mix that is an alcoholic pre-mix, wherein the dispenser is adapted to dispense an aliquot of the first pre-mix and an aliquot of the second pre-mix, such that the aliquots commingle. Upon commingling, the aliquots of the first pre-mix and second pre-mix chemically react and generate an antimicrobial alcoholic foam.

In certain embodiments, a first pump 110 may be in fluid communication with the first reservoir 102 through the inlet passage 106, and a second pump 112 may be in fluid communication with the second reservoir 104 through the inlet passage 108. First and second pumps 110 and 112 may be any type of pump known to those skilled in the art and suitable for conveying the first and second liquid pre-mix components from the first and second reservoirs 102 and 104. In one or more embodiments, the pumps 110 and 112 may both be positive displacement pumps. The first and second pumps 110 and 112 discharge the first and second pre-mix components through outlet passages 114 and 116, respectively. In certain embodiments, the output or displacement of the first and second pumps 110 and 112 may be adjustable to vary the rate of fluid flow therethrough. While the exemplary dispenser 100 shown and described includes first and second pumps 110 and 112, it is also contemplated that a single pump may be used, and may be in fluid communication with both the first and second reservoirs 102 and 104.

The outlet passages 114 and 116 may each extend to a mixing nozzle 118 where the first and second pre-mix components are commingled to form an antimicrobial alcoholic foam composition. The features and dimensions of the mixing nozzle 118 may be adjusted to vary the volume of each pre-mix aliquot, as well as the rate of mixing and commingling of the first and second pre-mix components. The mixing nozzle 118 includes a dispensing passage 120 through which the antimicrobial alcoholic foam composition is dispensed.

In certain embodiments, the first and second pumps 110 and 112 may be adjusted to produce substantially the same flow rate of the first and second pre-mix components therethrough. In other embodiments, the pumps 110 and 112 may be adjusted to provide different flow rates, and in certain embodiments, the pre-mix components may be dispensed sequentially.

In certain embodiments, the first and second pumps 110 and 112 may be adjusted to select substantially the same aliquot volume for the first and second pre-mix components. In other embodiments, the pumps 110 and 112 may be adjusted to provide different aliquot volumes.

In one or more embodiments, the first and second pumps 110 and 112 may be adapted to dispense a single dose of foam composition upon actuation. In the same or other embodiments, the first and second pumps 110 and 112 may be adapted to produce a continuous flow of the antimicrobial alcoholic foam composition upon actuation.

In one or more embodiments, the pre-mix components may be dispensed in selected proportions. In one or more embodiments, the size of the aliquots dispensed may be selected to provide an advantageous molar ratio of the acid to the carbonate. In one or more embodiments, the aliquots of the aqueous phase and the alcoholic phase are selected such that molar ratio of the acid to the carbonate is from about 0.5:1 to about 1:0.5, in other embodiments from about 0.6:1 to about 1:6, in other embodiments, from about 0.8:1 to about 1:0.8.

In one or more embodiments, the relative amount of the aqueous and alcohol pre-mix aliquots may be selected to provide a calculated yield of at least about 1 gram (g) carbon dioxide ($CO_2$) per 100 g of the combined aliquots, in other embodiments at least about 2 g, in other embodiments at least about 3 g, in other embodiments at least about 4 g $CO_2$ per 100 g of the combined aliquots.

In one or more embodiments, the size of the aliquots dispensed and the relative amount of the aqueous and alcohol pre-mix aliquots may be selected to provide a desired lower alcohol concentration, based upon the total weight of the combined aliquots. In one or more embodiments, the lower alcohol concentration of the combined aliquots is at least about 50 wt. %, in other embodiments at least about 55 wt. %, in other embodiments, at least about 60 wt. %, in other embodiments at least about 62 wt. %, in other embodiments at least about 65 wt. %, in other embodiments at least about 70 wt. %.

Figure 2:
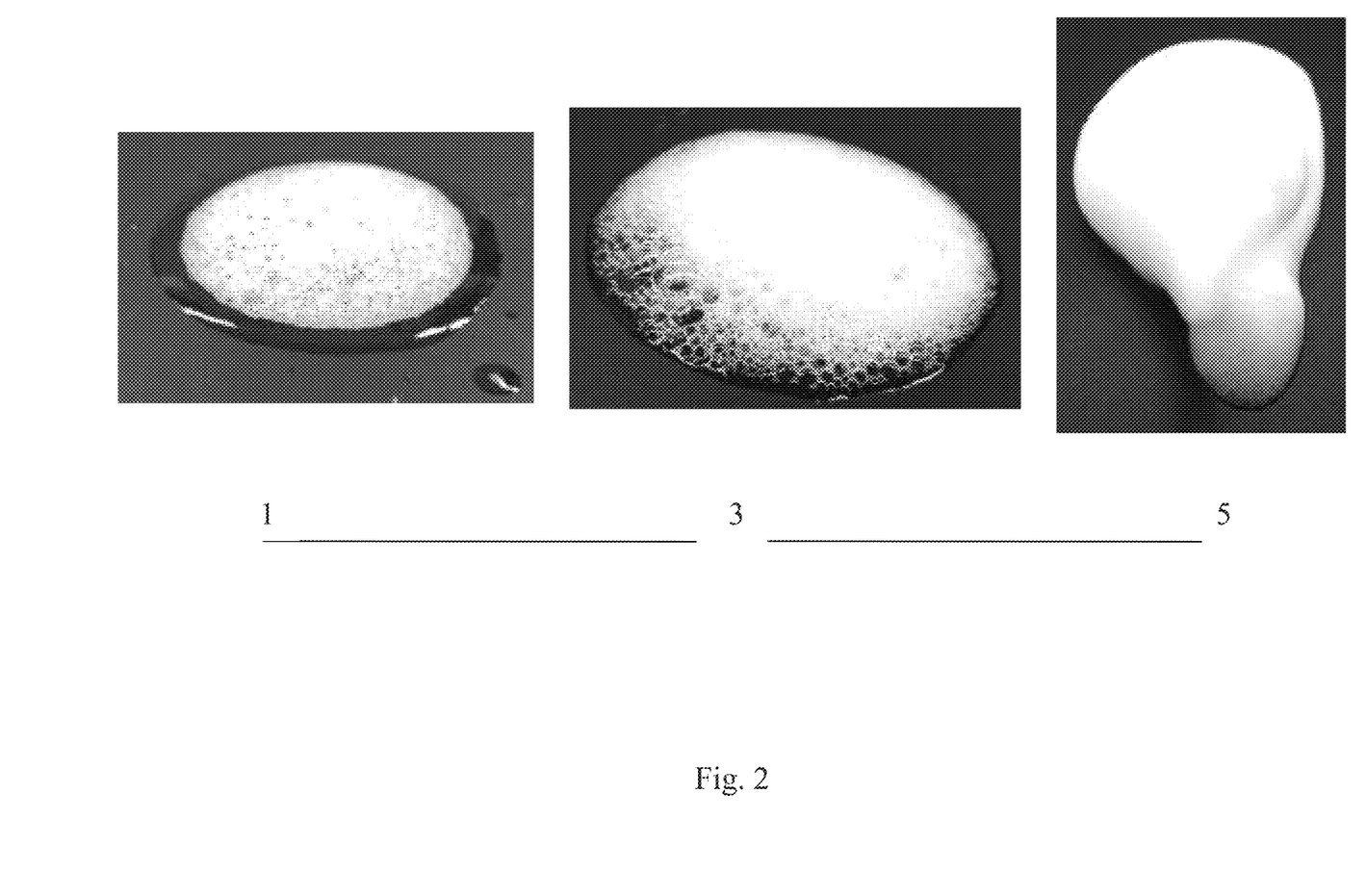
FIG. 2 is a pictorial depiction of the foam quality rating scale.

A rating scale was chosen to characterize the foam quality of foams produced according to the present invention. Advantageously, embodiments of the invention provide alcoholic foams, and should be considered to be quite distinct from mere effervescence. As shown in FIG. 2, a foam having a quality rating of at least 1 corresponds generally to a white foam having large bubbles, minimal foam height, and little or no structure. A foam having a quality rating of at least 3 corresponds generally to a white foam having medium to small size bubbles, minimal water ring, and noticeable foam height. A foam quality rating of about 5 generally corresponds to thick, dense foam with small, fine, frothy bubbles, in other words, having the quality of an aerosol foam. No known non-aerosol alcohol foam instant hand sanitizer products currently on the market have a foam quality rating of 5, according to this scale.

In one or more embodiments, the methods of the present invention produce stable foams, where foam stability is measured as the amount of time before the foam breaks down into a liquid, when dispensed onto a surface at standard temperature and pressure and observed over a period of time. In particular embodiments, the foam stability is at least about 1 minute, in other embodiments at least about 5 minutes, in other embodiments at least about 10 minutes, in other embodiments at least about 15 minutes, in other embodiments greater than 20 minutes.

In one or more embodiments, the foam is creamy and white, although it will be understood that pigments or dyes could be added to one or both of the pre-mixes to produce a colored foam. The bubbles are small and substantially uniform. The volume expansion of the foam, when compared to the volume of the combined pre-mix liquids, is significant, and in one or more embodiments is at least about 150%, in other embodiments at least about 200%, in other embodiments at least about 300%. In one or more embodiments, the foam expands upon the reaction of the acid and the carbonate to a final volume that is 1.5 to 5 times the combined liquid volume of the aqueous pre-mix and the alcoholic pre-mix.

The methods of the present invention can advantageously be employed to produce foams that contain high amounts of lower alcohols, such as ethanol, and which thus have significant antimicrobial efficacy.

In one or more embodiments, an antimicrobial foam composition of the present invention is applied topically to mammalian skin. In one embodiment, the methods of bringing the antimicrobial composition into contact with a microbe on human skin includes applying an amount of the composition to the skin, and allowing the composition to remain in contact with the skin for a suitable amount of time. In other embodiments, the composition may be spread over the surface of the skin, rubbed in, rinsed off, allowed to dry via evaporation, or wiped off. In other embodiments, an antimicrobial foam composition of the present invention is applied to an inanimate surface.

In order to demonstrate the practice of the present invention, the following examples have been prepared and tested. The examples should not, however, be viewed as limiting the scope of the invention. The claims will serve to define the invention.

EXAMPLES

The aqueous phase for the following examples was prepared by combining the water and the bicarbonate with mixing until the bicarbonate was fully dissolved. Ethanol and emulsifier, if any, were added and mixed until homogeneous.

The alcohol phase for the following examples was prepared as follows. The ethanol and acid were combined and mixed until the acid was fully dissolved. Emulsifier, if any, was added with mixing. The wax was heated until melted, and then added to the alcohol/acid solution and mixed until homogeneous.

Where the wax is identified as Emulsifying Wax, the emulsifying wax employed was Masurf Emulsifying Wax NF, available from Mason Surfactants Company. Product information from the supplier indicates that Masurf Emulsifying Wax NF contains cetearyl alcohol and polysorbate 60. Polawax A-31 was employed in some of the examples. Polawax A-31 is available from Croda Inc. Product information from the supplier indicates that Polawax A-31 is an emulsifying wax that contains a proprietary blend of a waxy component and an emulsifier.

All solutions were clear, homogeneous liquids, free from particulate or sediment. After the samples were prepared as described above, they were allowed to sit in closed containers for at least about 24 hours, and any instability, for example as evidenced by precipitation, was noted.

The samples were dispensed using dual pumps which delivered aliquots through a mixing nozzle in a ratio of 1:1 alcohol phase to water phase, on a volume basis. Approximately 0.6 milliliters (ml) of each phase were dispensed. The mixture exited the mixing nozzle and was deposited onto a clean, dry surface, whereupon the production of foam was virtually instantaneous. The foam was observed, and graded according to a pre-determined rating scale.

As shown in FIG. 2, a foam quality rating of 1 correlates to a watery white foam. This score can further be described as containing large bubbles and having no structure. A foam quality rating of 3 generally describes as a white foam having a minimal water ring. A foam having this score may further be described as containing medium to small size bubbles. A foam quality rating of 5 generally describes as a white foam that is thick and dense. A foam having this score may further be described as containing small, fine, frothy bubbles formed in or on the surface of a liquid.

Foams having a quality rating of 3 or better retained their shape and did not collapse to a liquid after at least about 15 minutes. That is, the foams produced were essentially unchanged after 15 minutes of observation.

The following wax products were employed in the Examples:

Polawax™ A-31-PA-(MH), available from Croda Inc., and described as a blend of fatty alcohol (cetearyl alcohol) and ethoxylated sorbitan ester.

Hallstar® TA-1618 Cetearyl Alcohol, available from The Hallstar Company, and described as Alcohols, $C^{14-18}$.

Masurf Emulsifying Wax NF, available from Mason Chemical Company, and described as a mixture of stearyl alcohol, 77 wt. %, polysorbate 60, 22 wt. %, and cetyl alcohol, 1 wt. %.

Cetyl stearyl alcohol NF, 95%, available from Jeen International Corporation, and described as 1-hexadecanol, 54.0-64.0 wt. %, and 1-octadecanol, 31.0-41.0 wt. %.

TABLE 1

| | | ALCOHOL PHASE | | | WATER PHASE | | | | | RESULTS | |
|---|---|---|---|---|---|---|---|---|---|---|---|
| | | Wax | Citric Acid | Ethanol | | Emuls. | Na Bicarb. | Water | Ethanol | | |
| EX.# | Wax | Amount (wt. %) | Amount (wt. %) | Amount (wt. %) | Emuls. Type | Amount (wt. %) | Amount (wt. %) | Amount (wt. %) | Amount (wt. %) | Foam Quality | Bubble Size |
| 1 | Emulsifying Wax NF | 6 | 3.7 | 90.3 | None | 0 | 9.5 | 90.5 | 0 | 4 | S |
| 2 | Cetearyl Alcohol NF | 4 | 3.3 | 92.7 | Polysorbate 20 | 4 | 9.5 | 86.5 | 0 | 4.5 | S |
| 3 | Emulsifying Wax NF | 4 | 5 | 91 | None | 0 | 7.8 | 75.2 | 15 | 0 | — |

TABLE 2

| | | ALCOHOL PHASE | | | WATER PHASE | | | | RESULTS | |
|---|---|---|---|---|---|---|---|---|---|---|
| | | Wax | Lactic Acid | Ethanol | | Emuls. | K Bicarb | Ethanol | Water | | |
| EX# | Wax Type | Amount (wt. %) | Amount (wt. %) | Amount (wt. %) | Emuls. Type | Amount (wt. %) | Amount (wt. %) | Amount (wt. %) | % Amount | Foam Quality | Bubble Size |
| 4 | Polawax A31 | 4 | 5 | 91 | Polysorbate 20 | 1 | 7.82 | 15 | 76.18 | 4 | S/M |
| 5 | Polawax A31 | 4 | 5 | 91 | Polysorbate 20 | 2 | 7 | 25.2 | 65.8 | 4 | S |
| 6 | Polawax A31 | 4 | 5 | 91 | None | 0 | 7.82 | 15 | 77.18 | 3.5 | S |
| 7 | Cetearyl Alcohol NF | 5 | 5 | 90 | None | 0 | 7.82 | 15 | 77.18 | 4 | S |
| 8 | Cetearyl Alcohol NF | 6 | 4 | 90 | Polysorbate 20 | 1 | 7.82 | 32 | 59.18 | 4 | S/Fine |
| 9 | Cetearyl Alcohol NF | 4 | 5 | 91 | None | 0 | 7.82 | 15 | 77.18 | 3.5 | S |
| 10 | Cetearyl Alcohol NF | 4 | 5 | 91 | Polysorbate 20 | 1 | 7.82 | 15 | 76.18 | 3.5 | S/M |
| 11 | Cetearyl Alcohol NF | 5 | 5 | 90 | Polysorbate 124 | 1 | 7.82 | 15 | 76.18 | 3.5 | S |
| 12 | Emulsifying Wax NF | 6 | 5 | 89 | Polysorbate 20 | 2 | 7 | 25.2 | 65.8 | 3.5 | S |

TABLE 3

| | | ALCOHOL PHASE | | | WATER PHASE | | | | RESULTS | |
|---|---|---|---|---|---|---|---|---|---|---|
| | | Wax | Acid Type/ | Ethanol | | Emuls. | K Bicarb | Ethanol | Water | | |
| EX# | Wax Type | Amount (wt. %) | Amount (wt. %) | Amount (wt. %) | Emuls. Type | Amount (wt. %) | Amount (wt. %) | Amount (wt. %) | % Amount | Foam Quality | Bubble Size |
| 13 | Emulsifying Wax NF | 5 | Citric/5 | 90 | Polysorbate 20 | 2 | 7.82 | 32 | 58.18 | 4 | S/M |
| 14 | Polawax A31 | 4 | Citric/5 | 91 | Polysorbate 20 | 1 | 7.82 | 26 | 59.18 | 4.5 | S |
| 15 | Cetearyl Alcohol NF | 6 | Lactic/4 | 90 | Polysorbate 20 | 1 | 7.82 | 32 | 59.18 | 4 | S/Fine |

TABLE 4

| | | ALCOHOL PHASE | | | WATER PHASE | | | | RESULTS | |
|---|---|---|---|---|---|---|---|---|---|---|
| | | Wax | Citric Acid | Ethanol | | Emuls. | K Bicarb | Ethanol | Water | | |
| EX # | Wax Type | Amount (wt. %) | Amount (wt. %) | Amount (wt. %) | Emuls. Type | Amount (wt. %) | Amount (wt. %) | Amount (wt. %) | % Amount | Foam Quality | Bubble Size |
| COMPARATIVE A | Emulsifying Wax NF | 5 | 0 | 90 | Polysorbate 20 | 1 | 7.82 | 15 | Q.S. | 0 | — |
| COMPARATIVE B | Emulsifying Wax NF | 5 | 5 | 90 | Polysorbate 20 | 1 | 0 | 15 | Q.S. | 0 | — |
| COMPARATIVE C | none | — | 5 | 90 | Polysorbate 20 | 1 | 7.82 | 15 | Q.S. | 0 | some effervescence |
| 16 | Emulsifying Wax NF | 5 | 5 | 90 | Polysorbate 20 | 1 | 7.82 | 15 | Q.S. | 4 | S/M |

TABLE 5

| | | ALCOHOL PHASE | | | WATER PHASE | | | | |
|---|---|---|---|---|---|---|---|---|---|
| | | Wax | Citric Acid | Ethanol | | Emuls. | K Bicarb | Ethanol | Water |
| EX # | Wax Type | Amount (wt. %) | Amount (wt. %) | Amount (wt. %) | Emuls. Type | Amount (wt. %) | Amount (wt. %) | Amount (wt. %) | % Amount | Foam Quality |
| 17 | Cetyl Alcohol NF | 2 | 5 | 93 | none | 0 | 7.82 | 15 | 77.18 | 1 |
| 18 | Cetyl Alcohol NF | 3 | 5 | 92 | none | 0 | 7.82 | 15 | 77.18 | 1.5 |
| 19 | Cetyl Alcohol NF | 4 | 5 | 91 | none | 0 | 7.82 | 15 | 77.18 | 2.5 |

TABLE 6

| | | ALCOHOL PHASE | | | WATER PHASE | | | | RESULTS | |
|---|---|---|---|---|---|---|---|---|---|---|
| | | Wax | Citric Acid | Ethanol | | Emuls. | K Bicarb | Ethanol | Water | | |
| EX # | Wax Type | Amount (wt. %) | Amount (wt. %) | Amount (wt. %) | Emuls. Type | Amount (wt. %) | Amount (wt. %) | Amount (wt. %) | % Amount | Foam Quality | Bubble Size |
| 20 | Stearyl Alcohol NF | 2 | 5 | 93 | none | 0 | 7.82 | 15 | 77.18 | 1 | L |
| 21 | Stearyl Alcohol NF | 3 | 5 | 92 | none | 0 | 7.82 | 15 | 77.18 | 1 | L |

TABLE 7

| | | ALCOHOL PHASE | | | WATER PHASE | | | | RESULTS | |
|---|---|---|---|---|---|---|---|---|---|---|
| | | Wax | Citric Acid | Ethanol | | Emuls. | K Bicarb | Ethanol | Water | | |
| EX # | Wax Type | Amount (wt. %) | Amount (wt. %) | Amount (wt. %) | Emuls. Type | Amount (wt. %) | Amount (wt. %) | Amount (wt. %) | % Amount | Foam Quality | Bubble Size |
| 22 | Emulsifying wax NF | 4 | 5 | 91 | Poloxamer 124 | 2 | 7.82 | 15 | 75.18 | 3.5 | S/M |
| 23 | Polawax A31 | 4 | 5 | 91 | Polysorbate 20 | 1 | 7.82 | 15 | 76.18 | 3.5 | M |
| 24 | Cetearyl Alcohol NF | 5 | 5 | 90 | Poloxamer 124 | 2 | 7.82 | 15 | 75.18 | 3 | S/M |

TABLE 8

| | | ALCOHOL PHASE | | | WATER PHASE | | | | RESULTS | |
|---|---|---|---|---|---|---|---|---|---|---|
| | | Wax | Citric Acid | Ethanol | | Emuls. | K Bicarb | Ethanol | Water | | |
| EX # | Wax Type | Amount (wt. %) | Amount (wt. %) | Amount (wt. %) | Emuls. Type | Amount (wt. %) | Amount (wt. %) | Amount (wt. %) | % Amount | Foam Quality | Bubble Size |
| 26 | Cetearyl Alcohol | 4 | 5 | 90 | Polysorbate 20 | 1 | 7.82 | 15 | 77.18 | 3.5 | S/M |

In Example 3, the sodium bicarbonate was not soluble in the water phase when 15 wt. % ethanol was present. Therefore, no foam was formed. As can be seen from Examples 13, 14 and 15, when potassium bicarbonate is employed, higher amounts of alcohol can be present in the aqueous phase, and excellent foam quality is still achieved.

Experiments similar to those shown above were performed using, as the waxy component, one of the following: lanette wax, hydrogenated jojoba oil, glyceryl stearate, sunflower wax, and synthetic candelilla wax (beeswax). Perhaps due to solubility issues, where the waxes were insoluble or only sparingly soluble in the alcohol phase, no foam was produced.

Advantageously, the methods of the present invention are useful to produce high quality stable alcoholic foams, without the need for mixing the product with air, passing the liquid through a mesh or screen, aerosol propellants, or pressurized packaging.

Various modifications and alterations that do not depart from the scope and spirit of this invention will become apparent to those skilled in the art. This invention is not to be duly limited to the illustrative embodiments set forth herein.

What is claimed is:

1. A method of preparing an antimicrobial alcoholic foam composition, the method comprising the steps of:
   providing a dispenser having a first reservoir containing a first liquid pre-mix that is an aqueous pre-mix, a second reservoir containing a second liquid pre-mix that is an alcoholic pre-mix;
   dispensing an aliquot of said aqueous pre-mix, wherein said aqueous pre-mix comprises a carbonate and water;
   dispensing an aliquot of said alcoholic pre-mix, wherein said alcoholic pre-mix comprises at least 50 wt. % of a $C_{1-6}$ alcohol, based upon the total weight of the alcoholic pre-mix, a waxy component, and an acidic component;
   commingling said aliquot of said aqueous pre-mix and said aliquot of said alcoholic pre-mix, whereupon said aliquots of said aqueous pre-mix and said alcoholic pre-mix chemically react and generate an antimicrobial alcoholic foam.

2. The method of claim 1 where the acidic component is selected from the group consisting of hydrochloric acid, nitric acid, phosphoric acid, phosphonic acid, boric acid, sulfuric acid, adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, and 2,5 furandicarboxylic acid, tartaric acid, malic acid, gluconic acid, fumaric acid, ascorbic acid, citric acid, isocitric acid, lactic acid, tartronic acid, oxalic acid, salicylic acid, malonic acid, potassium bitartrate, calcium phosphate, sodium aluminum phosphate, sodium aluminum sulfate, monosodium phosphate, disodium pyrophosphate, calcium lactate, calcium sulfate, calcium phosphate, sodium aluminum phosphate, sodium aluminum sulfate, monosodium phosphate and disodium pyrophosphate, and mixtures thereof.

3. The method of claim 1 wherein the acidic component is selected from the group consisting of citric acid, lactic acid, malic acid, tartaric acid, salicylic acid, oxalic acid, and mixtures thereof.

4. The method of claim 1 wherein the acidic component is citric acid.

5. The method of claim 1 wherein the amount of acidic component is at least 0.02 equivalent weights of acid per 100 g of combined aqueous pre-mix and alcoholic pre-mix.

6. The method of claim 1 wherein the amount of acidic component is from 0.5 to about 2 times the number of equivalent weights of carbonate present in the aqueous pre-mix.

7. The method of claim 1 wherein the amount of acidic component is the stoichiometric amount of acid required to produce at least 0.02 moles of carbon dioxide per 100 g of combined aqueous pre-mix and alcoholic pre-mix.

8. The method of claim 1 wherein the carbonate is selected from the group consisting of sodium carbonate, potassium carbonate, lithium carbonate, sodium bicarbonate, potassium bicarbonate, calcium bicarbonate, ammonium bicarbonate, and mixtures thereof.

9. The method of claim 1 wherein the carbonate is potassium bicarbonate.

10. The method of claim 1 wherein the amount of carbonate is an effective amount.

11. The method of claim 1 wherein the amount of carbonate is the stoichiometric amount of carbonate required to yield at least 0.02 moles of carbon dioxide per 100 g of combined aqueous pre-mix and alcoholic pre-mix.

12. The method of claim 1 wherein the aqueous pre-mix is a saturated solution with respect to the carbonate.

13. The method of claim 1 wherein the waxy component is selected from the group consisting of carnauba wax, ouricury wax, Japan wax, cork fiber wax, sugarcane wax, paraffin waxes, lignite waxes, microcrystalline waxes, lanolin wax, ozokerite, polyethylene wax, silicone waxes, plant waxes, $C_{8-24}$ fatty alcohols, $C_{8-24}$ fatty acids, glycerides that are solid at room temperature, blends of a $C_{8-24}$ fatty alcohol with an ethoxylated $C_{8-24}$ fatty alcohol, blends of a $C_{8-24}$ fatty alcohol and a non-ionic surfactant, and mixtures thereof, with the proviso that the wax is at least sparingly soluble in a lower alcohol at standard temperature and pressure.

14. The method of claim 1 wherein the waxy component is an emulsifying wax.

15. The method of claim 1 wherein the waxy component is present in an amount of at least 0.2 wt. %, based upon the total weight of the alcoholic pre-mix.

16. The method of claim 1 wherein the waxy component is present in an amount of at least 0.1 wt. %, based upon the total weight of the combined alcoholic pre-mix and aqueous pre-mix.

17. The method of claim 1 wherein the aqueous pre-mix further comprises an emulsifier selected from the group consisting of polysorbate, polaxamer, polyethoxylated siloxane polymer, or a mixture thereof.

18. The method of claim 1 wherein the alcoholic pre-mix further comprises an emulsifier selected from the group consisting of polysorbate, poloxamer, polyethoxylated siloxane polymer, or a mixture thereof.

19. The method of claim 18 wherein the emulsifier is a poloxamer.

20. The method of claim 1 wherein the aqueous pre-mix may further comprise up to about 49 wt. % $C_{1-6}$ alcohol.

21. The method of claim 1 wherein the foam expands upon the reaction of the acid and the carbonate to a final volume that is 1.5 to 5 times the combined liquid volume of the aqueous pre-mix and the alcoholic pre-mix.

22. The method of claim 1 wherein the foam is stable for at least 1 minute at room temperature and pressure.

23. A method of preparing a non-aerosol antimicrobial alcoholic foam composition, the method comprising the steps of:
providing a dispenser having a first reservoir containing a first liquid pre-mix that is an aqueous pre-mix, a second reservoir containing a second liquid pre-mix that is an alcoholic pre-mix;
dispensing an aliquot of said aqueous pre-mix, wherein said aqueous pre-mix comprises a carbonate and water;
dispensing an aliquot of said alcoholic pre-mix, wherein said alcoholic pre-mix comprises at least 50 wt. % of a $C_{1-6}$ alcohol, based upon the total weight of the alcoholic pre-mix, a waxy component, and an acidic component;
commingling said aliquot of said aqueous pre-mix and said aliquot of said alcoholic pre-mix, whereupon said aliquots of said aqueous pre-mix and said alcoholic pre-mix chemically react and generate an antimicrobial alcoholic foam;
wherein the foam expands upon the reaction of the acid and the carbonate to a final volume that is 1.5 to 5 times the combined liquid volume of the aqueous pre-mix and the alcoholic pre-mix.

24. The method of claim 23, where the acidic component is selected from the group consisting of hydrochloric acid, nitric acid, phosphoric acid, phosphonic acid, boric acid, sulfuric acid, adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, and 2,5 furandicarboxylic acid, tartaric acid, malic acid, gluconic acid, fumaric acid, ascorbic acid, citric acid, isocitric acid, lactic acid, tartronic acid, oxalic acid, salicylic acid, malonic acid, potassium bitartrate, calcium phosphate, sodium aluminum phosphate, sodium aluminum sulfate, monosodium phosphate, disodium pyrophosphate, calcium lactate, calcium sulfate, calcium phosphate, sodium aluminum phosphate, sodium aluminum sulfate, monosodium phosphate and disodium pyrophosphate, and mixtures thereof.

25. The method of claim 23, wherein the acidic component is selected from the group consisting of citric acid, lactic acid, malic acid, tartaric acid, salicylic acid, oxalic acid, and mixtures thereof.

26. The method of claim 23, wherein the acidic component is citric acid.

27. The method of claim 23, wherein the amount of acidic component is at least 0.02 equivalent weights of acid per 100 g of combined aqueous pre-mix and alcoholic pre-mix.

28. The method of claim 23, wherein the amount of acidic component is from 0.5 to about 2 times the number of equivalent weights of carbonate present in the aqueous pre-mix.

29. The method of claim 23, wherein the amount of acidic component is the stoichiometric amount of acid required to produce at least 0.02 moles of carbon dioxide per 100 g of combined aqueous pre-mix and alcoholic pre-mix.

30. The method of claim 23, wherein the carbonate is selected from the group consisting of sodium carbonate, potassium carbonate, lithium carbonate, sodium bicarbonate, potassium bicarbonate, calcium bicarbonate, ammonium bicarbonate, and mixtures thereof.

31. The method of claim 23, wherein the carbonate is potassium bicarbonate.

32. The method of claim 23, wherein the amount of carbonate is an effective amount.

33. The method of claim 23, wherein the amount of carbonate is the stoichiometric amount of carbonate required to yield at least 0.02 moles of carbon dioxide per 100 g of combined aqueous pre-mix and alcoholic pre-mix.

34. The method of claim 23, wherein the aqueous pre-mix is a saturated solution with respect to the carbonate.

35. The method of claim 23, wherein the waxy component is selected from the group consisting of carnauba wax, ouricury wax, Japan wax, cork fiber wax, sugarcane wax, paraffin waxes, lignite waxes, microcrystalline waxes, lanolin wax, ozokerite, polyethylene wax, silicone waxes, plant waxes, $C_{8-24}$ fatty alcohols, $C_{8-24}$ fatty acids, glycerides that are solid at room temperature, blends of a $C_{8-24}$ fatty alcohol with an ethoxylated $C_{8-24}$ fatty alcohol, blends of a $C_{8-24}$ fatty alcohol and a non-ionic surfactant, and mixtures thereof, with the proviso that the wax is at least sparingly soluble in a lower alcohol at standard temperature and pressure.

36. The method of claim 23, wherein the waxy component is an emulsifying wax.

37. The method of claim 23, wherein the waxy component is present in an amount of at least 0.2 wt. %, based upon the total weight of the alcoholic pre-mix.

38. The method of claim 23, wherein the waxy component is present in an amount of at least 0.1 wt. %, based upon the total weight of the combined alcoholic pre-mix and aqueous pre-mix.

39. The method of claim 23, wherein the aqueous pre-mix further comprises an emulsifier selected from the group consisting of polysorbate, polaxamer, polyethoxylated siloxane polymer, or a mixture thereof.

40. The method of claim 23, wherein the alcoholic pre-mix further comprises an emulsifier selected from the group consisting of polysorbate, poloxamer, polyethoxylated siloxane polymer, or a mixture thereof.

41. The method of claim 23, wherein the emulsifier is a poloxamer.

42. The method of claim 23, wherein the aqueous pre-mix may further comprise up to about 49 wt. % $C_{1-6}$ alcohol.

* * * * *